(12) United States Patent
Eibl

(10) Patent No.: US 8,889,624 B2
(45) Date of Patent: Nov. 18, 2014

(54) THROMBIN-FREE COMPOSITION CONTAINING FREEZE-DRIED, VIRALLY INACTIVATED FXIA AND SERPINS AND/OR KININOGEN

(75) Inventor: Johann Eibl, Vienna (AT)

(73) Assignee: Bio & Bio Licensing SA, Luxembourg (LU)

( * ) Notice: Subject to any disclaimer, the term of this patent is extended or adjusted under 35 U.S.C. 154(b) by 294 days.

(21) Appl. No.: 13/254,451

(22) PCT Filed: Sep. 16, 2010

(86) PCT No.: PCT/AT2010/000339
§ 371 (c)(1),
(2), (4) Date: Sep. 1, 2011

(87) PCT Pub. No.: WO2011/032195
PCT Pub. Date: Mar. 24, 2011

(65) Prior Publication Data
US 2011/0318330 A1 Dec. 29, 2011

(30) Foreign Application Priority Data
Sep. 16, 2009 (EP) ..................................... 09540173

(51) Int. Cl.
*A61K 38/36* (2006.01)
(52) U.S. Cl.
CPC ..................................... *A61K 38/36* (2013.01)
USPC ....................................................... 514/13.7
(58) Field of Classification Search
CPC .................................................... A61K 38/36
See application file for complete search history.

(56) References Cited

U.S. PATENT DOCUMENTS

| | | | |
|---|---|---|---|
| 4,160,025 A | 7/1979 | Eibl et al. | |
| 4,495,278 A * | 1/1985 | Thomas | 435/5 |
| 5,792,623 A * | 8/1998 | Turecek | 435/68.1 |
| 2005/0192223 A1 | 9/2005 | Eibl et al. | |
| 2006/0009376 A1 * | 1/2006 | Eibl | 514/2 |

FOREIGN PATENT DOCUMENTS

| | | |
|---|---|---|
| AT | 350726 B | 6/1979 |
| EP | 0225160 B1 | 6/1987 |
| WO | 2004011023 A | 2/2004 |
| WO | 2004/089297 A2 | 10/2004 |
| WO | WO 2005/049070 * | 6/2005 |

OTHER PUBLICATIONS

Enzyme Research Laboratories, Human Factor Xla, http://www.enzymeresearch.com/catalog_2/h_factorXla.html 2 pages, retrieved Nov. 9, 2013, (2004).*
Scott et al., "Cleavage of Human High Molecular Weight Kininogen by Factor Xla in Vitro", J.Biological Chemistry 260 (19) : 10856-10863 (1985).*
Astermark et al. A randomized comparison of bypassing agents in hemophilia complicated by an inhibitor: the FEIBA NovoSeven Comparative (FENOC) Study. Blood, 2007;109:546-551.
Brown S, Haemostasis from bench to bedside. Haemophilia. 2002; 8:1-9.
Hedner U, et al. Use of human factor VIIa in the treatment of two hemophilia A patients with high-titer inhibitors. J Clin Invest. 1983;71:1836-41.
Kurczynski E, et al. Activated prothrombin concentrate for patients with factor VIII inhibitors. N. Engl J Med, 1974;291:164-7.
Roberts H, et al. The use of recombinant factor VIIa in the treatment of bleeding disorders. Blood. 2004;104:3858-3864.
Sun Mao-Fu et al. Identification of amino acids in the factor XI apple 3 domain required for activation of factor IX. Dec. 17, 1999.
Sun Mao-Fu et al: "Identification of amino acids in the factor XI apple 3 domain required for activation of factor IX", XP002614346, Dec. 17, 1999 Database accession No. PREV200000078995.
Toomey John R El AL: "The Factor IX Gla-Domain is Required for Factor IX Activation by Factor Xla.", XP002614347, Database accession No. PREV200300335609 * abstract, vol. 100, No. 11, Nov. 16, 2002, page Abstract No. 1009, 44th Annual Meeting of the American Society of Hematology; Philadelphia, PA, USA; Dec. 6-10, 2002, ISSN: 0006-4971.

* cited by examiner

*Primary Examiner* — Sandra Saucier
(74) *Attorney, Agent, or Firm* — Mashoff Brennan

(57) ABSTRACT

A virally safe, thrombin-free factor-XIa concentrate or a coagulation factor concentrate which contains factor XIa as an active pharmaceutical ingredient and which is obtained by fractionation of plasma or serum or by genetic engineering and is suitable for the treatment of coagulation disorders attributable to diminished and/or delayed thrombin formation.

13 Claims, 5 Drawing Sheets

FIG.1: Thrombelastogram of Platelet-Rich Normal Plasma with TF Dilutions of 1:30000 and 1:300000
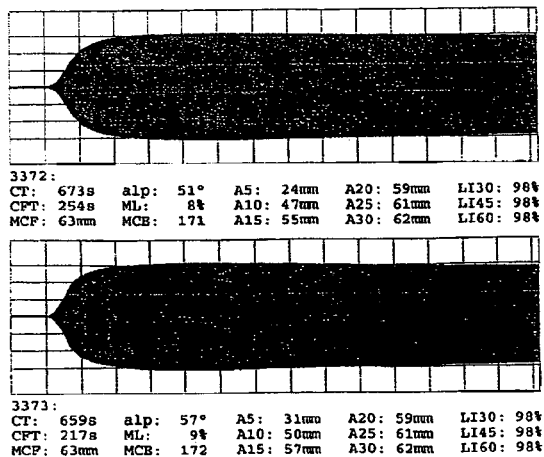
FIG.2: Thrombelastogram of Platelet-Rich Factor-VIII Inhibitor Plasma with TF Dilutions of 1: 30000 and 1:300000
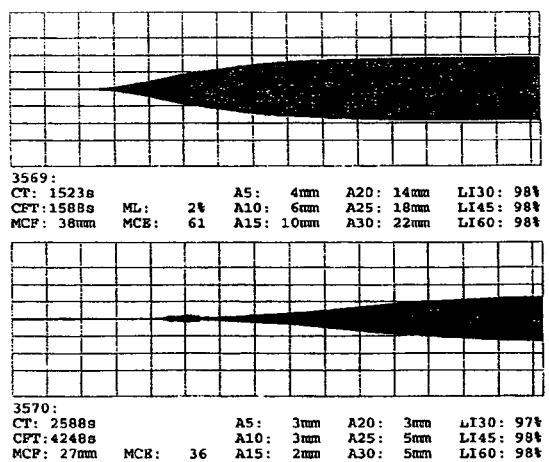

FIG.3: Thrombelastogram of Platelet-Rich Factor-VIII Inhibitor Plasma with TF Dilution of 1:30000 and Additions of Factor VIIa
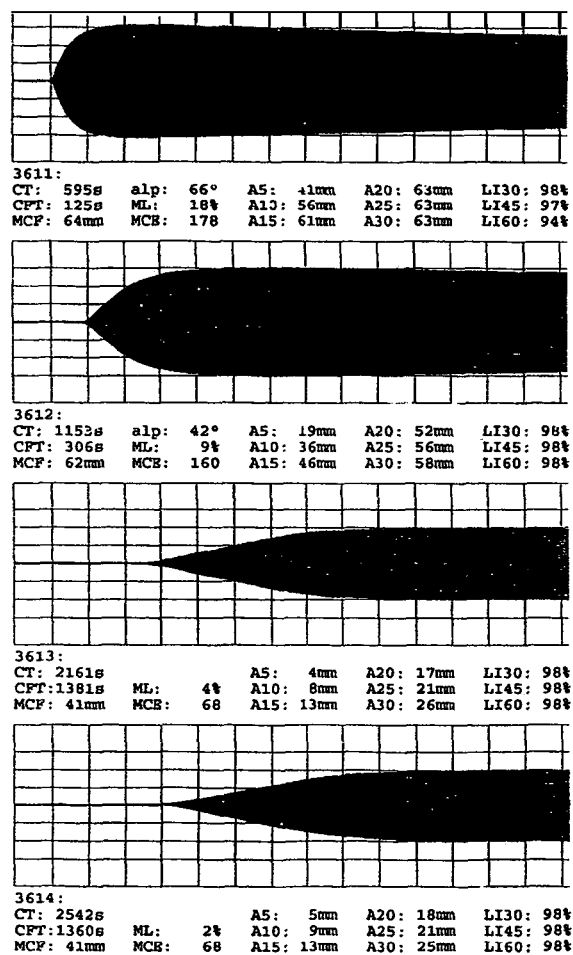

FIG.4: Thrombelastogram of Platelet-Rich Factor-VIII Inhibitor Plasma with TF Dilution of 1:300000 and Additions of Factor VIIa
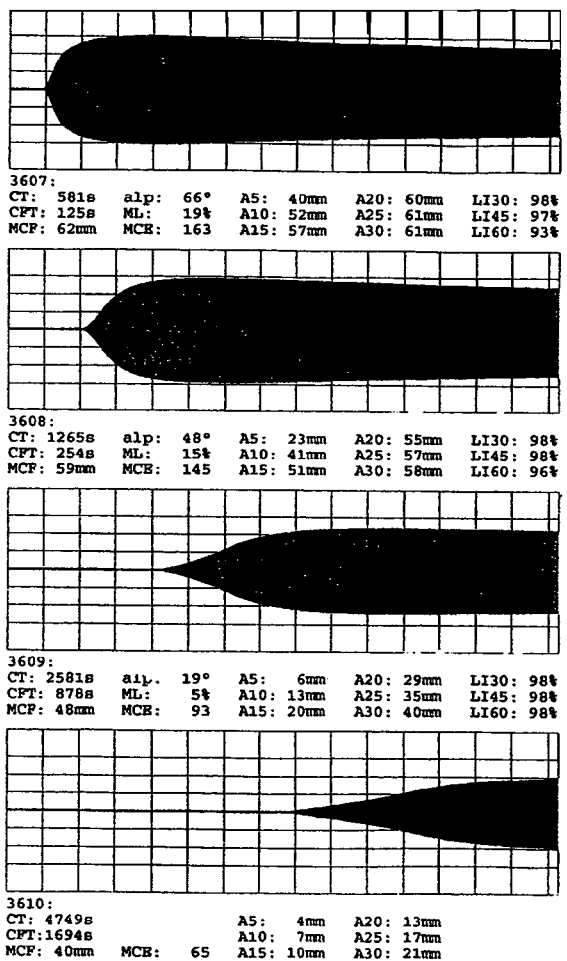

FIG.5: Thrombelastogram of Platelet-Rich Factor-VIII Inhibitor Plasma with TF Dilution of 1:30000 and Additions of Factor XIa
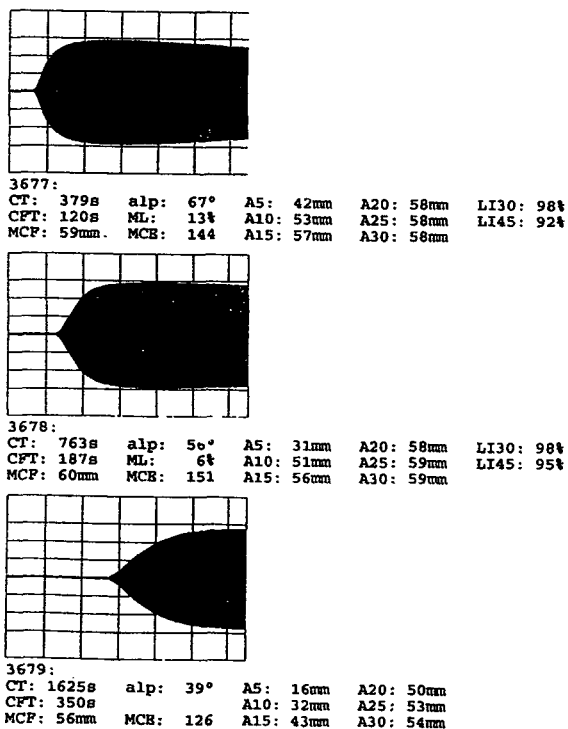

FIG.6: Thrombelastogram of Platelet-Rich Factor-VIII Inhibitor Plasma with TF Dilution of 1:300000 and Additions of Factor XIa
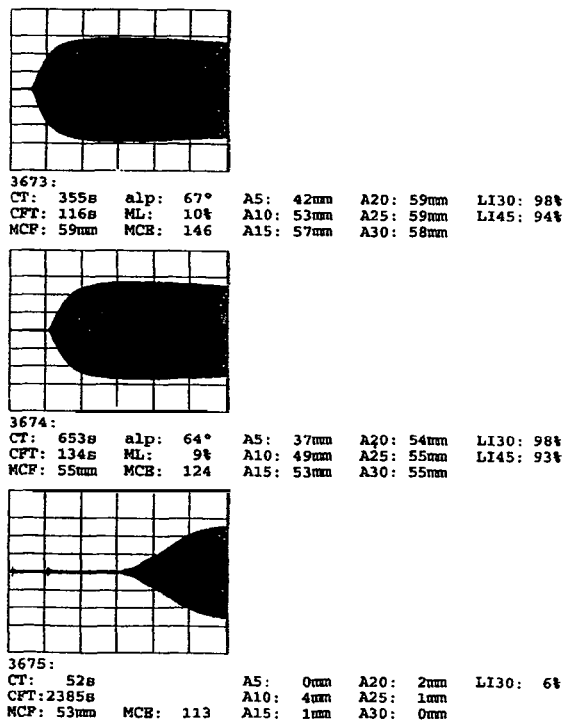

THROMBIN-FREE COMPOSITION CONTAINING FREEZE-DRIED, VIRALLY INACTIVATED FXIA AND SERPINS AND/OR KININOGEN

BACKGROUND OF INVENTION

The present invention relates to a virally safe, thrombin- and pyrogen-free factor-XIa concentrate and to the use of a virally safe factor-XIa concentrate for the production of a pharmaceutical composition for the treatment of coagulation disorders.

Injuries of the organism may result in severe bleeding, with massive or even fatal blood loss. The organism is protected against severe blood loss by a hemostatic mechanism, which causes the exiting blood to coagulate, whereby the bleeding is controlled and the wound is closed. Research into the hemostatic process has been conducted during the last century, and although a basic understanding has been gained, is still ongoing.

According to the present understanding, disruption of vessels exposes substances which trigger blood coagulation, so that a hemostatic plug can be formed. The plug contains a network of fibrin and platelets, the platelet count exceeding the blood count 20 to 200-fold. The plug adheres to, and closes, the injured site. The importance of the role of platelets in hemostasis can be illustrated by the fact that patients with afibrinogenemia do not tend to bleed profusely, while patients with severe thrombocytopenia may suffer non-controllable bleedings.

The blood coagulation process involves individual blood components such as blood cells, microparticles, and blood plasma. The coagulation of blood occurs when fibrinogen as a soluble protein in the blood plasma is converted into insoluble fibrin by the enzymatic action of thrombin, an enzyme which splits fibrinogen into soluble fibrin monomers and fibrinopeptides A and B. The fibrin monomers aggregate to fibrin monomer complexes and finally to insoluble fibrin. In patients with normal blood coagulation, only approximately one fourth of the fibrinogen that was present in the amount of blood from which a clot is formed, is converted into fibrin. The further conversion of fibrinogen in the clot depends on the amount of thrombin generated therein (Kumar R, et al.)

Thrombin results from prothrombin by activation at the end of the enzyme cascade, where coagulation factors which are pro-enzymes are activated into activated coagulation factors which are enzymes in a predetermined order. Coagulation factors which are not pro-enzymes are pro-co-factors, which are converted enzymatically into co-factors. Each co-factor enhances the enzymatic conversion of a specific pro-enzyme into an enzyme (Mann K G, et al.).

The enzyme cascade which results in thrombin can be divided into four different pathways, the extrinsic, the intrinsic, and the common pathway, and in addition, the so-called contact-phase. The present understanding is that on an injured blood vessel, tissue factor, a cell-bound lipoprotein, initiates the extrinsic pathway by forming a complex with factor VIIa, and this complex activates factor X into factor Xa. Factor Xa forms another enzyme complex, called prothrombinase, which generates thrombin from prothrombin. This pathway, where factor Xa generates thrombin, is called the common pathway. The generation of factor Xa by the extrinsic pathway is soon interrupted by tissue factor pathway inhibitor. As a consequence, only small amounts of thrombin can be generated via the extrinsic and common pathways. The small amounts of thrombin, however, trigger the activation of the intrinsic pathway. By activation of the intrinsic pathway large amounts of factor X are activated, so that thrombin is generated in excess via the common pathway. To what extent platelets and the contact phase contribute to the activation of the intrinsic pathway, is still a matter of discussion (Walsh P).

In patients who suffer from severe coagulation disorders all their lives, even minor traumatic events may cause uncontrollable bleedings. Such patients have either inherited deficiencies of specific coagulation factors or acquired the deficiencies in the course of their lives. Bleeding disorders of this type are referred to as hemophilia. Most patients who suffer from severe hemophilia have a deficiency of coagulation factor VIII (Brown S).

Coagulation factor VIII is a pro-cofactor, which is enzymatically transformed into a cofactor via the intrinsic pathway. This cofactor accelerates the activation of factor X by tenase, an activated factor-VIII-IX complex, dramatically, so that an excess of thrombin can be formed via the common pathway. Thrombin converts fibrinogen and factor XIII into fibrin and factor XIIIa, respectively. Factor XIIIa, a transglutaminase, causes the formed fibrin to cross-link, which results in an increased adhesion of the coagulated blood to the wound edges. In the further course, TAFI, a proenzyme, is activated into TAFIa. TAFIa splits off the receptor peptide for plasmin from fibrin, rendering the cross-linked fibrin more resistant against lysis. These enzymatic processes lead to an increased stability of the clot, an increase in its elasticity, and an increase in its resistance to lysis.

Patients with factor VIII deficiency form hemostatic plugs with difficulty only. If they do form a plug, the plug is fragile and will dissolve within short by fibrinolytic processes, the reason being that the intrinsic pathway is impaired in the clot and only an insufficient amount of thrombin is generated in the clot (Sixma J, et al.).

Once it became possible to produce concentrates of coagulation factor VIII as part of the fractionation of human plasma, bleeders with factor VIII deficiency could be treated so successfully that their average lifespan of 15 years could be prolonged to that of a normal person.

It was gradually understood that a considerable percentage of patients that had been treated successfully with factor VIII concentrates turned refractory to the very products they were treated with. Investigations of the phenomenon led to the conclusion that those patients developed antibodies against the homologous factor VIII they had received, which largely inhibited the function of factor VIII in the coagulation process. Such bleeders, thereafter referred to as factor VIII inhibitor patients, suffered the same fate as factor VIII deficient patients prior to the availability of factor VIII concentrates (van den Berg H, et al.). The same pathological process occurs in factor IX deficient patients as they become refractory to substitution therapy with factor IX concentrates.

In the 1970's, factor VIII inhibitor patients were treated unsuccessfully with different hemostatic medicinal products. It became known that only certain batches of products containing prothrombin complex were effective. Medicinal products containing prothrombin complex contain several vitamin-K-dependent coagulation factors, predominantly factors II, IX, X, and VII, and, depending upon the manufacturing process, those factors may in part be present in activated form (Kelly P, et al. and Kurczynski E, et al.). The Baxter Group then succeeded in manufacturing such partly activated prothrombin complex preparations and in marketing them by the trade name of "Autoplex" (Fekete L, et al.).

About the same time, Immuno AG succeeded in developing a product for the treatment of the same group of patients, which bridges the impairment in the coagulation cascade and normalizes coagulation (Eibl J, et al. and Turecek P, et al.). This product was introduced by the name of "FEIBA". After the Baxter Group acquired Immuno AG in 1998, Baxter discontinued the production of Autoplex and continued producing and distributing FEIBA worldwide.

In the early 1980's, Novo Nordisk A/S introduced a recombinant factor VIIa product (Hedner U, et al.) by the name of "NovoSeven" (Hedner U) for the treatment of patients with factor VIII and factor IX inhibitors and other bleeding disorders. (Roberts H, et al.) Thus, two companies became leaders in parenteral medicinal products for the treatment of bleeders with inhibitors. As far as estimates allow, about 90% of the market today is covered by FEIBA and NovoSeven, amounting to annual sales of 1.5 billion Dollars, with NovoSeven accounting for approximately 60% and FEIBA approximately 40%.

The most recent publication about the efficacy of FEIBA and NovoSeven as assessed in a comparative multicenter trial reports no significant difference in the percentage of patients who stopped bleeding within six hours of treatment. Neither has their been a difference in the rate of adverse events, particularly thromboses (Astermark J, et al.).

Jan Astermark et al have shown that treatment with those products produced rapid hemostasis in only half of the patients. In about 25 percent of the patients, hemostasis occurred only after repeated doses of either Feiba or NovoSeven, and only after a prolonged period of time. Another 25 percent had either insufficient hemostasis, or the bleeding could not be controlled at all. The frequency of adverse events, particularly thromboses, was the same in either group.

Since the introduction and successful use of these pharmaceutical preparations, there has been speculation about their mode of action. In parallel, and irrespective thereof, the understanding of the coagulation process itself has changed and improved over the last 30 years. Nevertheless, no uniform or ultimate opinion has been reached about their mode of action (Roberts H, et al.).

SUMMARY OF INVENTION

The objective of the invention is to provide a medicinal product for parenteral use which is efficacious in achieving fast and sustained control of bleeding in patients with coagulation disorders, and in particular, patients with inhibitors to factors VIII or IX, and one that will be safer than the products presently on the market in terms of adverse events, even if given in high doses. In addition, the cost of producing it should not be higher than those of the products presently on the market. The improvement of the coagulation process in these patients should consist not only in a shortening of the coagulation and bleeding times but be primarily achieved in the clot itself, where an amount of thrombin must be generated to compare with that in a healthy person.

For a product to be administered parenterally, it is important that it contains no thrombin activity and/or does not generate thrombin prior to administration. Pure factor XI concentrates do not contain thrombin and do not generate thrombin either during storage nor during freeze-drying, reconstitution or prior to administration. When other, non-activated and activated coagulation factors are added for formulation, great care needs to be used to maintain this absence of thrombin. The latter is of utmost importance for the safety of the product, the parenteral application of thrombin bearing the potential of creating thromboses or DIC. When thrombin is manufactured for topical application, factor XI or factor XIa may be used in the process of manufacture and may, if so desired, be removed in the further course of manufacturing without the topical activity of thrombin affecting hemostasis in any negative manner.

In most patients suffering from hemophilia, be it because of a lack of factor VIII or factor IX, the intrinsic coagulation pathway is strongly down-regulated. This is particularly true of patients who have antibodies against one or the other of these factors. In persons with normal blood coagulation, more than 90% of the thrombin is generated by the intrinsic pathway, three quarters of the thrombin being formed in the clot itself. In patients with hemophilia, the amount of thrombin generated in the clot is insufficient, so that they cannot form blood clots which persist for an extended period of time as would be necessary to sustain hemostasis.

According to the invention, an alternative intrinsic pathway can be generated by activated factors of the contact phase in the presence of fibrin and/or fibrin monomer complexes. When factor XI, completely or partially activated, is added to blood, platelet-rich or platelet-poor plasma of patients with hemophilia, thrombin generation in the clot is normalized. This improves the quality of the formed clot considerably, which reflects in an increase in the elasticity module and the resistance against lysis.

Virus inactivation by solvent/detergent is best accomplished prior to chromatographic purification of the factor or factors, so that the added solvent/detergent can be separated. Further virus removal can be achieved by nanofiltration, ultrafiltration, and/or heating in freeze-dried state. The virus safe activated, partially activated or non-activated factors or co-factors and their derivatives are then stored at refrigerator temperature or deep-frozen prior to formulation of the medicinal product.

To stabilize factors XII and XI and their derivatives, high molecular weight kininogen, a co-factor of the contact phase, preferably bradykinin-poor kininogen, is added. In the same manner, the long chain high molecular weight kininogen split off by reduction, can be used.

In order to accelerate the coagulation process and hemostasis, activated and non-activated factors of the prothrombin complex may be added during formulation.

Such activated or non activated clotting factors as well as formulated Factor XIa concentrates must be free of thrombin or must not generate thrombin prior to application.

Treatment with factors, in particular with activated factors of the contact phase, may be accompanied by a risk of thrombosis. To reduce this potential risk, low avid serpins or other appropriate homologous protease inhibitors are added to the coagulation factor concentrates of the contact phase to prevent activation during storage and/or application.

The addition of low-avid serpins or other appropriate protease inhibitors may prevent autoactivation of non-activated coagulation factors, to the extent present in the medicinal product, during storage and/or application.

Therefore the invention is directed to a thrombin-free factor-XIa concentrate or a thrombin-free coagulation factor concentrate containing factor XIa for the manufacture of a pharmaceutical preparation which does not form thrombin during storage, and for the manufacture of a parenterally applicable drug product which does not form thrombin during or after freeze-drying, storage and reconstitution.

A preferred embodiment of the pharmaceutical preparation according to the present invention contains serpins and/or high molecular weight kininogen or its split products.

A further preferred embodiment of the pharmaceutical preparation is nanofiltered to improve viral safety, either before or after formulation, preferably by nanofilters with a pore diameter of ≤20 nm or is filtered by a 1000 kDalton ultrafilter.

The pharmaceutical preparation according to the invention is preferably rendered virally safe by treatment with solvent/detergent and subsequent removal of solvent and detergent.

The pharmaceutical preparation according to the invention may be filled under sterile and pyrogen-free conditions and may be freeze-dried and virally inactivated by heating the filled, freeze-dried pharmaceutical preparations at no less than 90° C. and no more than 140° C. for 30 to 180 minutes.

The invention is also directed to a thrombin-free factor-XIa concentrate or thrombin-free coagulation factor concentrate containing factor XIa, characterized in that it is obtained by fractionation of plasma or serum or by genetic engineering.

The thrombin-free factor-XIa concentrate or thrombin-free coagulation factor concentrate containing factor XIa according to the invention or the pharmaceutical preparation according to the invention are preferably virally safe and pyrogen-free.

The invention is also directed to a diagnostic kit for the determination of the amount of factor-XIa concentrate which is necessary to normalize prolonged blood coagulation in a reference factor-VIII inhibitor plasma and in blood samples of patients with coagulation disorders.

The thrombin-free factor-XIa concentrate or the thrombin-free coagulation factor concentrate containing factor XIa according to the invention as described above can be used as an active ingredient for the production of a medicinal drug product for the treatment of coagulation disorders.

BRIEF DESCRIPTION OF FIGURES

Thrombelastographic determination of coagulation defects and their normalization is known in the art. In the following, the thromboelastograph ROTEG 05 by the company Pentapharm GmbH, Kreillerstraβe 21, D-81673 Munich, Germany, was used.

Description of the thrombelastographic measuring process: The measuring cells of the thrombelastograph by the company Pentapharm GesmbH, Munich consists of a cuvette and a plug, which are inserted into the measuring device. The cuvette is filled with the materials to be tested prior to insertion, heated to 37° C., and the plug is inserted accordingly. Measurement time is 60-150 min, and the process of clot formation is monitored using the following parameters:
  a. Coagulation time (CT). CT is the time span from the start point to the occurrence of an amplitude of 2 mm.
  b. Clot formation time (CFT). CFT is the time span in which the amplitude rises from 2 to 20 mm.
  c. α-angle. α-angle is the parameter which results from the angle of the mid line and the tangent of the curve of the amplitude.
  d. Clot formation rate (CFR). CFR is the widest angle of the slope of the curve of the amplitude between its tangent and the midline.
  e. Maximum clot formation (MCF). MCF is the greatest distance of the curve of the amplitude from the midline.
  f. MCF-time (MCF-t). MCF-t is the time span from the time point of coagulation to the time point of achieving maximum clot firmness.
  g. Maximum lysis (ML). ML is defined by the greatest difference in height between the MCF and the lowest amplitude resulting from lysis.
  h. Lysis time (LT). LT is the time span from the time point of coagulation onset to the time point of clot dissolution.
  i. Lysis onset (LOT). LOT is the time span from the time point of coagulation onset to the time point of lysis onset.

240 μl of platelet-rich normal plasma or inhibitor plasma are pipetted into the cuvette. Other additions of solutions or reagents must not exceed 80 μl, and the volume per cuvette must not exceed 320 μl. If the additions are less than 80 μl, the cuvette is filled up to 320 μl with isotonic saline.

FIG. 1: Thrombelastogram 3372 was obtained by the addition of a dilution of relipidated TF of 1:30000 to platelet-rich normal plasma. Thrombelastogram 3373 was obtained by the addition of a dilution of relipidated TF of 1:300000 to platelet-rich normal plasma.

FIG. 2: Thrombelastogram 3569 was obtained by the addition of a dilution of relipidated TF of 1:30000 to factor-VIII inhibitor plasma. Thrombelastogram 3570 was obtained by the addition of a dilution of relipidated TF of 1:300000 to factor-VIII inhibitor plasma.

FIG. 3: Thrombelastogram 3611 was obtained by the addition of a dilution of relipidated TF of 1:30000 to platelet-rich inhibitor plasma, to which also 10 U factor VIIa were added. Thrombelastogram 3612 was obtained by the addition of a dilution of relipidated TF of 1:30000 to platelet-rich inhibitor plasma, to which also 1 U factor VIIa was added. Thrombelastogram 3613 was obtained by the addition of a dilution of relipidated TF of 1:30000 to platelet-rich inhibitor plasma, to which also 1/10th U factor VIIa was added. Thrombelastogram 3614 was obtained by the addition of a dilution of relipidated TF of 1:30000 to platelet-rich inhibitor plasma, to which also 1/100th U factor VIIa was added.

FIG. 4: Thrombelastogram 3607 was obtained by the addition of a dilution of relipidated TF of 1:300000 to platelet-rich inhibitor plasma, to which also 10 U factor VIIa were added. Thrombelastogram 3608 was obtained by the addition of a dilution of relipidated TF of 1:300000 to platelet-rich inhibitor plasma, to which also 1 U factor VIIa was added. Thrombelastogram 3609 was obtained by the addition of a dilution of relipidated TF of 1:300000 to platelet-rich inhibitor plasma, to which also 1/10th U factor VIIa was added. Thrombelastogram 3610 was obtained by the addition of a dilution of relipidated TF of 1:300000 to platelet-rich inhibitor plasma, to which also 1/100th U factor VIIa was added.

FIG. 5: Thrombelastogram 3677 was obtained by the addition of a dilution of relipidated TF of 1:30000 to platelet-rich inhibitor plasma, to which also a 1:10 dilution of factor XIa concentrate was added. Thrombelastogram 3678 was obtained by the addition of a dilution of relipidated TF of 1:30000 to platelet-rich inhibitor plasma, to which also a 1:100 dilution of factor XIa concentrate was added. Thrombelastogram 3679 was obtained by the addition of a dilution of relipidated TF of 1:30000 to platelet-rich inhibitor plasma, to which also a 1:1000 dilution of factor XIa concentrate was added.

FIG. 6: Thrombelastogram 3673 was obtained by the addition of a dilution of relipidated TF of 1:300000 to platelet-rich inhibitor plasma, to which also a 1:10 dilution of factor XIa concentrate was added. Thrombelastogram 3674 was obtained by the addition of a dilution of relipidated TF of 1:300000 to platelet-rich inhibitor plasma, to which also a 1:100 dilution of factor XIa concentrate was added. Thrombelastogram 3675 was obtained by the addition of a dilution of relipidated TF of 1:300000 to platelet-rich inhibitor plasma, to which also a 1:1000 dilution of factor XIa concentrate was added.

EXAMPLES

1. Thrombin- and pyrogen-free virus safe Factor XIa concentrates 10 l source plasma will be frozen, thawed and the cryo-precipitate formed after complete thawing will be removed. The supernatant will be mixed with 500 g washed DEAE-Sephadex-A50 and stirred for 30 min at 4° C. Sephadex will be removed by filtration and the supernatant may be used in the production for further plasma fractions. The Sephadex will be washed 3 times at 4° C. with 10 l 0.01 molar phosphate buffer, pH 7.8 containing 1% NaCl. Factor XI will be eluted with the same phosphate buffer (2 l) containing 3% NaCl. The eluate will be lightly stirred at 30° C. for 12 h with 20 g Tween-80 and 6 g trinitrobutylphospate (TNBP). Tween-80 and TNBP will be removed by—multiple if necessary—adsorption and elution of Factor XI on DEAE-Sephadex-A50. It will be advantageous to wash the Sephadex adsorbed Factor XI with a 1% buffered NaCl solution to removal of the solvent and detergents.

The last Sephadex eluate will be diluted 1+4 with 0.01 molar phosphate buffer, pH 8.2. The Factor XI in this diluted eluate will be adsorbed onto a DEAE-Sephadex-A50 column. After washing the column with 0.1 molar phosphate buffer pH 7.8 containing 1% NaCl, a linear gradient elution step will be performed; whereby the NaCl gradient will be prepared by mixing a 0.01 molar phosphate buffer solution, pH 7.5-7.8 with the same phosphate buffer containing 3% NaCl. Fractions of 100 ml each will be collected and the fractions containing Factor XI will be used for further processing.

Factor XI can be activated by Factor XIIa, Factor XIa, trypsin, thrombin and other agents. In case of this example with virus safe commercially available thrombin and heparin the optimal conditions for activating Factor XI in the concentrates will be determined in preliminary experiments at room temperature over 3 h. While the preliminary experiments are being performed, the Factor XI concentrate can be kept frozen at −20° C. to avoid bacterial contamination. After the optimal amounts of thrombin and heparin for activation have been determined, the frozen Factor XI concentrate will be thawed and activated with the determined amounts of thrombin and heparin at 10° C. for 4 h.

The Factor XIa containing solution will be depleted of thrombin by repeating adsorption and elution of Factor XIa on DEAE-Sephadex-A50, in such a way that the last DEAE-Sephadex-eluate should not contain more than 0.1 units of thrombin per ml (i.e. 0.01 units of thrombin per 100 µl), which is regarded as "thromin-free" in the sense of the present description and claims. The concentration steps of Factor XIa concentrates including the removal of solvent detergents as well as the concentration of Factor XIa activating agents can also be performed by a gradient elution of Factor XIa with other resins adsorbing Factor XIa such as QAE-Sepharose, SP-Sepharose or Concanavalin-A-Sepharose.

For viral safety the factor XIa concentrate will be further processed by nano filtration applying a 20 nm pore filter. Before this filtration it may be necessary to clarify the solution by a 75 nm and a 35 nm pore filter as well as by a protein permeable ultrafilter. It might be advantages to ultracentrifuge the solution in a flow through centrifuge with a minimum of 50.000 rpm. After adequate formulation the Factor XIa will be filtered through a sterile filter of 100 or 200 nm pore size and the sterile bulk solution will be filled in final containers and freeze dried. The humidity content of the freeze dried Factor XIa concentrate should be 0.8-2.0% water. The freeze dried Factor XIa in the final containers will undergo heat treatment after airtight sealing for 30 min at 100° C. as an additional virus inactivation step. This is a preferred embodiment of the invention.

2. Proof of absence of thrombin in the Factor XIa concentrate:
   100 µl of factor a XIa concentrate will be mixed with 200 µl of 0.1% fibrinogen solution; both solutions will be adjusted at a pH 7.8 and a temperature of 37° C. The exact time of mixing will be recorded and the mixture will be observed for 250 sec to register clotting and/or flocculation. In parallel 100 µl of 0.1 unit thrombin per ml solution will be mixed with 200 µl of 0.1% fibrinogen solution at 37° C. pH 7.5 and under keeping the temperature at 37° C. will be observed for 250 sec. Within this time period complete clotting of the fibrinogen added is expected to occur. The factor XIa concentrate is determined as "thrombin free" if after mixing with fibrinogen neither clotting nor flocculation occurs and if in parallel the 0.01 unit thrombin with fibrinogen clots.

3. Estimation of the Factor XIa activity:
   Activity will be assessed with the chromogenic substrate S2366 at 37° C. in a buffered solution of pH 8.3. Dilutions of a Factor XI concentrate or a Factor XIa concentrate will be determined in a volume of 200 µl. 15 µl of 30 mmol S2366 solution will be added and adjusted with TRIS buffer pH 8.3 to a total volume of 300 µl and mixed. The tests will be performed in micro titer plates and each well covered with 2 drops of mineral oil. Extinction will be followed for 2 h and the activity of Factor XIa in the concentrate will be estimated based on the dose-response-curve of a Factor XIa reference preparation.

4. Platelet-rich normal or factor-VIII inhibitor plasma:
   Platelet-rich plasma from healthy donors was centrifuged at 4000 revolutions per minute for 5 minutes, the supernatant plasma was removed, and the platelets were washed with a phosphate glucose buffer of pH 6.5 three times. The last sediment was suspended in platelet-poor normal plasma or platelet-poor factor-VIII inhibitor plasma, and the platelet suspension was adjusted to a platelet count between two and three million platelets per µl. This platelet concentrate was diluted prior to use 1:10 with platelet-poor normal plasma or platelet-poor factor-VIII inhibitor plasma. The platelet-poor factor-VIII inhibitor plasma must have a content of at least 100 Bethesda Units per ml.
   In the sample for thrombelastogram 3372 (FIG. 1), 240 µl of platelet-rich normal plasma were mixed with 10 µl of a TF dilution of 1:30000. After the addition of 50 µl of isotonic saline, coagulation was initiated by the addition of 20 µl of a 0.2 M CaCl2 solution.
   The same procedure was used with sample 3373 (FIG. 1), except that the TF solution used was diluted 1:300000.
   As can be seen from the thrombelastogram (FIG. 1), CT was 673 sec, and after the addition of an amount of TF to $1/10^{th}$, was 659 sec, resulting in a non-significant difference. MCF was 63 ml with both samples. Equally, the difference in the α-angle was not significant.

When platelet-rich factor-VIII inhibitor plasma was used, there were significant differences with different TF concentrations. The CT in samples 3569 and 3570 (FIG. 2) was 1523 sec. in both when a TF dilution of 1:30000 was used and was much delayed compared to platelet-rich normal plasma, and was still considerably prolonged in sample 3570, which gave 2588 sec.

Also MCF in samples 3569 and 3570, which was 38 mm and 27 mm, respectively, was much reduced compared to samples 3372 and 3373. These results suggest that the TF dilution of 1:300000 gives the greatest difference between the coagulation behavior of normal plasma and that of platelet-rich inhibitor plasma.

The glucose-phosphate buffer used had the following composition:
sodium citrate dihydrate 2.2%
citric acid 0.8%
glycose monohydrate 2.42%

RecombiPlas Tin-Hemosil lot NO574097G from Instr. Lab. was used. The normal plasma was freshly obtained donor plasma. The factor-VIII inhibitor plasma was lot 824 and was supplied by Biomex.

5. Normalization of the thrombelastographic coagulation parameters of platelet-rich factor-VIII inhibitor plasma by the addition of factor-VIIa concentrate using TF dilutions of 1:30000 and 1:300000:

As can be seen from FIG. 3, the coagulation parameters of platelet-rich factor-VIII inhibitor plasma were only normalized by the addition of 10 U of factor VIIa (thrombolastogram 3611). The addition of 1 U (3612), $1/10^{th}$ (3613) and $1/100^{th}$ (3614) of a U (prolonged the coagulation time to 1153 sec, 2161 sec, and 2542, respectively. 10 U of factor VIIa normalized the MCF completely to 64 mm, while all additions with lower VIIa gave a gradual MCF shortening.

When a higher TF dilution of 1:300000 was used (FIG. 4), practically all coagulation parameters could be normalized with the addition of 10 U (3607) of factor VIIa. However, the difference in the CT was more pronounced than with a lower TF dilution, the addition of 1 U (3608), of $1/10^{th}$ (3609) and $1/100^{th}$ (3610) of a U prolonging CT to 1265 sec, 2581 sec, and 4749 sec, respectively.

The factor VII concentrate used was lot SU61347 by Novo Nordisk.

6. Normalization of the thrombelastographic coagulation parameters of platelet-rich factor-VIII inhibitor plasma by the addition of a factor-XIa concentrate using TF dilutions of 1:30000 and 1:300000:

The same samples and reagents were used as in Example 2, except that an S/D virus inactivated, nanofiltered factor XIa concentrate was used instead of a factor VIIa concentrate, which was heated in freeze-dried state at 100° C. for 30 min and which yielded a solution of factor XIa of 1100 U per ml after reconstitution with WFI.

As can be seen from thrombelastogram 3677 (FIG. 5), the CT of 379 sec. was significantly shorter with $1/10^{th}$ of a U of factor XIa than that of normal plasma (FIG. 1: 3372). With 59 mm, the MCF was also in the normal range. The same was true for an addition of only $1/100^{th}$ of a U of factor XIa, which gave a CT in the normal range. See Sample 3678 (FIG. 5). As can be seen from sample 3679, only $1/1000^{th}$ of a U of factor XIa prolongs the CT to 1625 sec.

When the higher dilution of TF of 1:300000 was used along with factor XIa, the normalization of the coagulation parameters was even more pronounced than with factor VIIa concentrates.

References Cited

Astermark J, et al. A randomized comparison of bypassing agents in hemophilia complicated by an inhibitor: the FEIBA NovoSeven Comparative (FENOC) Study. Blood, 2007; 109:546-551.

Brown S, Haemostasis from bench to bedside. Haemophilia. 2002; 8:1-9 Eibl J et al., AT350726, 1976.

Fekete L, et al. 'Auto' factor IX concentrate: a new therapeutic approach to treatment of hemophilia A patients with inhibitors. International Congress of Hematology, Sao Paulo, 1972; 295 [Abstract].

Hedner U, EP0225160B1, 1986.

Hedner U, et al. Use of human factor VIIa in the treatment of two hemophilia A patients with high-titer inhibitors. J Clin Invest. 1983; 71:1836-41.

Kelly P, et al. Antihemophilic factor inhibitors. Management with prothrombin complex concentrates. JAMA, 1976; 236:2061-4.

Kumar R, et al. The Influence of Fibrinogen and Fibrin on Thrombin Generation—Evidence for Feedback Activation of the Clotting System by Clot Bound Thrombin. Thrombosis and Haemostasis 1994; 72:713-21.

Kurczynski E, et al. Activated prothrombin concentrate for patients with factor VIII inhibitors. N Engl J Med, 1974; 291:164-7.

Mann K G, et al. Blood Coagulation Dynamics in Haemostasis. Hämostaseologie 2009; 29:7-16.

Roberts H, et al. The use of recombinant factor VIIa in the treatment of bleeding disorders. Blood. 2004; 104:3858-3864.

Sixma J, et al. The haemostatic plug in haemophilia A: a morphological study of haemostatic plug formation in bleeding time skin wounds of patients with severe haemophilia A. British Journal of Haematology, 1984; 58:741-753.

Turecek P, et al. FEIBA: mode of action. Haemophilia. 2004; 10:(Suppl. 2):3-9 van den Berg, H, et al. Clinical Prediction Models for Inhibitor Development in Severe Hemophilia A. J. Thrombosis and Haemostasis, 2009; 7 (Suppl.1):98-102.

Walsh P. Roles of Platelets and Factor XI in the Initiation of Blood Coagulation by Thrombin. Thromb Haemost 2001; 86:75-82.

The invention claimed is:

1. A thrombin-free factor-XIa concentrate or a thrombin-free coagulation factor concentrate containing factor XIa for the manufacture of a pharmaceutical preparation which does not form thrombin during storage, and for the manufacture of a parenterally applicable drug product which does not form thrombin during or after freeze-drying, storage and reconstitution, which is produced under sterile and pyrogen-free conditions and is freeze-dried and virally inactivated by heating the filled, freeze-dried pharmaceutical preparations at no less than 90° C. and no more than 140° C. for 30 to 180 minutes, the pharmaceutical preparation further comprising serpins and/or high molecular weight kininogen or its split products.

2. The pharmaceutical preparation according to claim 1, wherein the thrombin-free factor-XIa concentrate or a thrombin-free coagulation factor concentrate containing factor XIa is nanofiltered to improve viral safety before formulation of the pharmaceutical preparation, or the pharmaceutical preparation is filtered after formulation thereof.

3. The pharmaceutical preparation according to claim 1, which is rendered virally safe by treatment with solvent/detergent and subsequent removal of solvent and detergent.

4. Thrombin-free factor-XIa concentrate or thrombin-free coagulation factor concentrate containing factor XIa according to claim 1, which is obtained by fractionation of plasma or serum or by genetic engineering.

5. A method of manufacturing a medicinal drug product for treatment of coagulation disorders, the method comprising:
provjding the thrombin-free factor-XIa concentrate or a thrombin-free coagulation factor concentrate containing factor XIa of claim 1; and
preparing a medicinal drug product from the thrombin-free factor-XIa concentrate or a thrombin-free coagulation factor concentrate containing factor XIa as an active ingredient.

6. The pharmaceutical preparation of claim 2, wherein the nanofiltering uses a nanofilter with a pore diameter of ≤20 nm.

7. The pharmaceutical preparation of claim 2, wherein the nano filtering uses a nanofilter is a 1000 kDalton ultrafilter.

8. A pharmaceutical preparation comprising:
a thrombin-free factor-XIa concentrate or a thrombin-free coagulation factor concentrate containing factor XIa which does not form thrombin during storage, wherein the pharmaceutical preparation is filled under sterile and pyrogen-free conditions and is freeze-dried and virally inactivated by heating the filled, freeze-dried pharmaceutical preparations at no less than 90° C. and no more than 140° C. for 30 to 180 minutes,
the pharmaceutical preparation further comprising serpins and/or high molecular weight kininogen or its split products.

9. The pharmaceutical preparation of claim 8, wherein the pharmaceutical preparation is configured as a parenterally applicable drug product which does not form thrombin during or after freeze-drying, storage and reconstitution.

10. The pharmaceutical preparation according to claim 8, wherein the thrombin-free factor-XIa concentrate or a thrombin-free coagulation factor concentrate containing factor XIa is nanofiltered to improve viral safety before formulation of the pharmaceutical preparation, or the pharmaceutical preparation is filtered after formulation thereof.

11. The pharmaceutical preparation of claim 10, wherein the nanofiltering uses a nanofilter with a pore diameter of ≤20 nm.

12. The pharmaceutical preparation of claim 10, wherein the nanofiltering uses a nanofilter is a 1000 kDalton ultrafilter.

13. The pharmaceutical preparation according to claim 1, which is rendered virally safe by treatment with solvent/detergent and subsequent removal of solvent and detergent.

* * * * *

UNITED STATES PATENT AND TRADEMARK OFFICE
CERTIFICATE OF CORRECTION

| | | |
|---|---|---|
| PATENT NO. | : 8,889,624 B2 | Page 1 of 1 |
| APPLICATION NO. | : 13/254451 | |
| DATED | : November 18, 2014 | |
| INVENTOR(S) | : Eibl | |

It is certified that error appears in the above-identified patent and that said Letters Patent is hereby corrected as shown below:

On the Title Page, item (74), under "Attorney, Agent, or Firm", in Column 2, Line 1,
    delete "Mashoff Brennan" and insert -- Maschoff Brennan --, therefor.

Signed and Sealed this
Thirty-first Day of March, 2015

Michelle K. Lee
*Director of the United States Patent and Trademark Office*